United States Patent
Lersch et al.

(10) Patent No.: US 7,858,580 B2
(45) Date of Patent: Dec. 28, 2010

(54) DERMATOLOGICAL COMPOSITIONS INCLUDING OLIGOPEPTIDES FOR INCREASING SKIN SENSITIVITY AND NEURONAL PERCEPTION

(75) Inventors: Peter Lersch, Dinslaken (DE); Mike Farwick, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 494 days.

(21) Appl. No.: 11/869,450

(22) Filed: Oct. 9, 2007

(65) Prior Publication Data

US 2008/0200400 A1   Aug. 21, 2008

(30) Foreign Application Priority Data

Oct. 7, 2006   (DE) .................... 10 2006 047 529

(51) Int. Cl.
    *A61K 38/00* (2006.01)
(52) U.S. Cl. .......................................... 514/2
(58) Field of Classification Search ............ None
    See application file for complete search history.

(56) References Cited

U.S. PATENT DOCUMENTS

| 5,492,894 A | 2/1996 | Bascom et al. |
| 2004/0132667 A1 | 7/2004 | Lintner |

FOREIGN PATENT DOCUMENTS

| DE | 10 2005 063 179 A1 | | 9/2006 |
| JP | 2002080497 | * | 3/2002 |
| WO | WO 03/068141 A2 | | 8/2003 |
| WO | WO 2005/048968 A1 | | 6/2005 |

OTHER PUBLICATIONS

Yanai et al. "Prolyl Endopeptidase Inhibitory Peptides in Wine," Biosci. Biotechnol. Biochem., 2003, 67, 380-382.*
Machine translation of JP2002080497, Mar. 2002.*
Yanai T. et al., "Prolyl Endopeptidase Inhibitory Peptides in Wine", Biosci. Biotechnol. Biochem. 67(2):380-382 (2003), XP002482367.
Biochemie; Berg. J.M., Tymoczko, J.L., Stryer L.; 5th edition; Spektrum Akademiseher Verlag; Heidelberg Berlin; 2003, p. 55; table 3.2.

* cited by examiner

*Primary Examiner*—Christina Bradley
(74) *Attorney, Agent, or Firm*—Scully, Scott, Murphy & Presser, P.C.

(57) ABSTRACT

The invention relates to dermatological compositions including at least one oligopeptide with a sequence of 4, 5 or 6 amino acids and/or a derivative thereof as means for increasing the sensitivity of skin, wherein the amino acid sequence comprises the dipeptide sequence Ile-Pro and/or Pro-Ile.

10 Claims, No Drawings

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial
<220> FEATURE:
<223> OTHER INFORMATION: synthetic peptide

<400> SEQUENCE: 1

Arg Pro Lys Pro Gln Gln Phe Phe Gly Leu Met
1               5                   10

<210> SEQ ID NO 2
```

```
<211> LENGTH: 5
<212> TYPE: PRT
<213> ORGANISM: Artificial
<220> FEATURE:
<223> OTHER INFORMATION: synthetic peptide

<400> SEQUENCE: 2

Val Glu Ile Pro Glu
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Tyr Pro Ile Pro Phe
1               5

<210> SEQ ID NO 4
<211> LENGTH: 4
<212> TYPE: PRT
<213> ORGANISM: Artificial
<220> FEATURE:
<223> OTHER INFORMATION: synthetic peptide

<400> SEQUENCE: 4

Ala Ile Pro Gln
1

<210> SEQ ID NO 5
<211> LENGTH: 4
<212> TYPE: PRT
<213> ORGANISM: Artificial
<220> FEATURE:
<223> OTHER INFORMATION: synthetic peptide

<400> SEQUENCE: 5

Gly Pro Ile Pro
1

<210> SEQ ID NO 6
<211> LENGTH: 4
<212> TYPE: PRT
<213> ORGANISM: Artificial
<220> FEATURE:
<223> OTHER INFORMATION: synthetic peptide

<400> SEQUENCE: 6

Ser His Pro Ile
1

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Arg Lys Pro Ile Pro
1               5

<210> SEQ ID NO 8
<211> LENGTH: 5
```

```
<212> TYPE: PRT
<213> ORGANISM: Artificial
<220> FEATURE:
<223> OTHER INFORMATION: synthetic peptide

<400> SEQUENCE: 8

Tyr Pro Ile Ser Leu
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Gly His Pro Ile Ser
1               5

<210> SEQ ID NO 10
<211> LENGTH: 6
<212> TYPE: PRT
<213> ORGANISM: Artificial
<220> FEATURE:
<223> OTHER INFORMATION: synthetic peptide

<400> SEQUENCE: 10

Gly Val Glu Ile Pro Ala
1               5

<210> SEQ ID NO 11
<211> LENGTH: 6
<212> TYPE: PRT
<213> ORGANISM: Artificial
<220> FEATURE:
<223> OTHER INFORMATION: synthetic peptide

<400> SEQUENCE: 11

Thr Lys Pro Ile Pro Arg
1               5

<210> SEQ ID NO 12
<211> LENGTH: 4
<212> TYPE: PRT
<213> ORGANISM: Artificial
<220> FEATURE:
<223> OTHER INFORMATION: synthetic peptide

<400> SEQUENCE: 12

Pro Ile Pro Phe
1
```

DERMATOLOGICAL COMPOSITIONS INCLUDING OLIGOPEPTIDES FOR INCREASING SKIN SENSITIVITY AND NEURONAL PERCEPTION

FIELD OF THE INVENTION

The invention relates to dermatological compositions and to the use of specific oligopeptides in such dermatological compositions for increasing skin sensitivity and neuronal perception via the skin.

BACKGROUND OF THE INVENTION

Being about 2 $m^2$, the skin (cutis) is the largest and most nerve-rich organ in the human body and performs numerous tasks with its layer structure of epidermis (upper skin), dermis (corium) and subcutis (lower skin). The skin protects the entire organism from pathogens or molecules, solar irradiation and drying out. In addition, however, oxygen and nutrients are absorbed via skin pores. The skin additionally serves to regulate and maintain body temperature.

As a result of a large number of different receptors—about 7 to 50 per $cm^2$—the human skin gains the ability to register highly diverse sensory impressions, ranging from temperature sensations via pain and itching to gentle touches. Coordinative information such as the position of body parts in space is also ascertained via skin receptors. Physical and/or chemical stimuli acting upon the organism are registered by the special receptors, and the information is passed to the brain in the form of neuronal activity via the peripheral nervous system. In the epidermis, for example, the Merkel cells have been identified as mechanoreceptors for touch and pressure sensations. Further important sensors are the Vater-Pacini corpuscles in the suboutis area which react to vibrations, and Meissner's touch corpuscles or touch disks at the epidermal-dermal border which are responsible for touch sensations. Further well-developed sensory organs in the region of the epidermis are the Ruffini corpuscles (stretch receptors), and the Krause corpuscles or end bulbs (mechanoreceptors). Intraepithelial nerve endings are sensitive nerve fibers in the skin which trigger sensations of warmth, cold, pain, touch and pressure.

A nociceptor (Latin nocere: to damage) is a receptor which reacts to impending or existing injury of the body tissue. The density of nociceptors in humans is greater than that of all other skin receptors. Distribution on the surface of the body is relatively even. The change in the stimulus threshold is brought about through the release of endogenous, chemical substances which make the nociceptors more sensitive and more receptive. Some of these substances are bradykinin, prostaglandin E2 and serotonin. In the event of damage (noxa), these substances are released. If the concentration of these substances exceeds a certain level, then it results in a pain reaction. However, even if, on account of the concentration, the pain threshold is not exceeded, a small amount of these substances suffices to increase the excitability of the nociceptors. The nociceptors are then more sensitive and the person is more likely to perceive pain, and to a greater extent. The pain substances not only bring about sensitization of the nerve ends, they also have an effect on the permeability of the vessel walls and cause a narrowing of the blood vessels. The overall chemical environment of the nociceptor is changed and increases its excitability.

In particular, peptides perform important functions in the human body and also in the skin as bioactive messengers, for example, as hormones, neurotransmitters or as neuromodulators. The neuropeptide class of substances plays an important role since these are short oligopeptides which often occupy a position between hormones and pure neurotransmitters. The neuropeptide class of substances function is also referred to as neuromodulatory since they can gradually assist or suppress the effect of other transmitters. In contrast to molecularly small transmitters, synthesis and transport are rather slow and sluggish. In addition, neuropeptides do not bind directly to ion channels and thus do not change the tension of the postsynaptic membrane, but act via receptors upon cell functions and upon the cell structure of the postsynaptic target cell.

There is a large number of scientific investigations that concentrate on the role of oligopeptides as messengers and as neuromodulators in the brain. Thus, in immunological investigations, it has been established that when sensory nerve endings are stimulated, neuropeptides are released which are essential for neuronal perception and stimulus conveyance in the brain. Substance P is one example of such a neuropeptide which has become known primarily as a pain and inflammation mediator. Substance P consists of 11 amino acids and belongs to the group of neurokinins and is foiined by nerve cells, but also by leukocytes. The amino acid sequence is Arg-Pro-Lys-Pro-Gln-Gln-Phe-Phe-Gly-Leu-Met-$NH_2$ (SEQ ID NO:1).

If an afferent nociceptor is highly excited, it releases substance P, which was firstly recognized as a neurotransmitter in pain receptors and pain-conducting C fibers. However, substance P also plays a role as a modulator in inflammation reactions and brings about considerable dilation of the blood vessels and increases the permeability of the vessel walls. Consequently, local perfusion of the tissue is increased. These processes also bring about an increase in the sensitivity of the nociceptor.

The effect of capsaicin, the alkaloid occurring naturally in paprika and chili (which is in chemical terms is a vanillylamide of 8-methyl-6-nonanoic acid), is also based on the intense stimulation of chemonociceptors in nerve cells. Capsaicin stimulates the nerve ends of certain nociceptors which normally recognize pain stimuli upon the action of heat or chemical stimuli. Capsaicin binds to the TRP channel TRPV1, which is also activated through an increase in the temperature. The painful (but only apparent) heating due to capsaicin is counteracted by the organism through release of substance P from intracellular storage vesicles. This leads acutely to membrane depolarization and, as a result of the increased perfusion of the tissue for the purpose of dissipating heat, local reddening results, as in the case of a slight burn.

Substance P antagonists are at the moment very much the focus of scientific research, for example, for pain therapy and as potential antidepressants.

The effect of substance P in the synaptic gap is ended by rapid peptidase-mediated degradation. Protection against degradation by various endopeptidases can be achieved through enzyme inhibitors. This phenomenon is the subject of current pharmaceutical investigations. Various classes of substances are being investigated for this purpose. Besides other oligopeptides, in more recent medical investigations, two proline-containing pentapeptides with the sequence Val-Glu-Ile-Pro-Glu (SEQ ID NO:2) and Tyr-Pro-Ile-Pro-Phe (SEQ ID NO:3) have been identified. It is assumed that these are able to inhibit prolyl-endopeptidase. This enzyme is suspected of being involved in the pathogenesis of Alzheimer's disease and senility via the degradation of various neuropeptides.

Thus, for example, Yanai, Sato and Suzuki disclose, in Biosci. Biotechnol. Biochem., 67 (2), 380 to 382, 2003, oligopeptides with the sequences Val-Glu-Ile-Pro-Glu and Tyr-Pro-Ile-Pro-Phe which are suitable for inhibiting the prolylendopeptidase.

The use of certain peptides and oligopeptides as agents to counter external signs of skin aging in skincare products is known, for example, from the applications listed below.

WO 2005/048968 discloses the use of a combination of tri- and tetrapeptides in cosmetic compositions in order to alleviate or to avoid topically visible changes in the skin, such as wrinkles and dark circles. The combination of the peptides described in WO 2005/048968 reportedly results in an increased production of collagen I, fibronectin, collagen IV and hyaluronic acid in skin cells.

WO 2003/7068141 discloses a cosmetic or dermopharmaceutical composition for reducing symptoms of skin slackening and skin aging. This prior art composition comprises a synergistic combination of at least two, preferably three, components which are selected from a) hesperidine or a derivative thereof
b) A.C.E. enzyme inhibitor dipeptides, and
c) oligopeptides $R_2$-$(AA)_n$-Pro-Arg-OH, where $(AA)_n$ is a peptide chain of amino acids or derivatives thereof, and n is between 1 and 3 and $R_2$=H or an alkyl chain with $C_2$ to $C_{22}$.

In U.S. Pat. No. 5,492,894, an oligopeptide having 3 to 6 amino acids is used in a topical composition for the cosmetic treatment of wrinkles, where three of the amino acids are selected, independently of one another, from Lys or Arg.

In more recent cosmetic formulations for topical application to the skin, the oligopeptides used exhibit a muscle-relaxing effect and can thus reduce or eliminate mimic wrinkles, such as so-called crow's feet, in the skin. One example of this is a hexapeptide, acetyl hexapeptide-3 (argireline). This oligopeptide can inhibit the nerve signal to the muscle contraction, namely the messenger acetylcholine, and thus superficially relax and smooth the skin by interrupting stimulus conveyance. Such formulations are used as alternatives to antiwrinkle treatments with injections of the nerve poison botulinum toxin A (Botox).

However, all of the formulations of the cosmetic or dermatological skincare products known in the prior art are aimed at improving the external appearance of aging skin.

None of the described substances or formulations assists or improves the skin in its function as sensory organ such as, for example, by improving neuronal perception via the skin.

The estimation as to whether aging phenomena of the skin are to be perceived more as a consequence of a physiological process or as a disease state differs depending on the cultural, social and psychological background. The characteristic features of aging skin include atrophy, dryness, roughness, development of wrinkles, loss of elasticity, pigment irregularities, a tendency to form multiple, mostly benign, new growths and increased likelihood of injury as a result of extensive structural and functional changes, which ultimately lead to a thinning of the skin layers and to a decrease in their function-bearing components. Neuronal perception of the skin is also decisively impaired by aging processes. Thus, for example, thermoregulation in aged skin is increasingly sluggish, i.e., the protective organisms of the body against loss of heat or overheating no longer function to the extent that they used to in young skin. This is a result of the ever diminishing ability of the vessels to dilate or to constrict.

SUMMARY OF THE INVENTION

The present invention provides dermatological compositions and the use of such dermatological compositions for supporting and improving neuronal perception of the skin.

Surprisingly, it has been found that the use of at least one oligopeptide with a sequence of 4 to 6 amino acids results in a dermatological composition that can support and improve neuronal perception of the skin.

The invention therefore provides dermatological compositions comprising at least one oligopeptide with a sequence of 4, 5 or 6 amino acids and/or a derivative thereof as means for increasing the sensitivity of the skin, wherein the amino acid sequence comprises the dipeptide sequence Ile-Pro and/or Pro-Ile.

DETAILED DESCRIPTION OF THE INVENTION

As stated above, the present invention provides dermatological compositions that can be used for supporting and improving neuronal perception of the skin. The inventive dermatological composition includes at least one oligopeptide with a sequence of 4, 5 or 6 amino acids and/or a derivative thereof as means for increasing the sensitivity of the skin, wherein the amino acid sequence comprises the dipeptide sequence Ile-Pro and/or Pro-Ile.

These are preferably pentapeptides or derivatives thereof.

The dipeptide sequence Pro-Ile is also called Pro-Ile motif in the description of the invention.

In one embodiment of the invention, the oligopeptides used for producing a dermatological composition are those in which the Ile-Pro motif or the Pro-Ile motif are preferably arranged in the 2 position or 3 position. For the purposes of the invention, 2 position means that they are arranged behind the first N-terminal amino acid of the oligopeptide sequence.

According to the invention, the term amino acid includes all naturally occurring amino acids, either in the D or L configuration, if optically active, and the known non-natural, synthetic and modified amino acids, such as, for example, homocysteine, 4-hydroxyproline, 5-hydroxylysine, gamma-aminobutyrate, orthinine, norleucine and p-valine. According to the invention, the amino acids can be used in optically pure form or as a racemic mixture.

For the purposes of the description of the invention, the three-letter code for the amino acids is used, where in sequences in principle from left to right firstly the N-terminal end and then the C-terminal end is indicated. This corresponds to the generally customary abbreviation of the amino acids, as is given, for example, in Biochemie; Berg, J. M., Tymoczko, J. L., Stryer L.; 5th edition; Spektrum Akademischer Verlag; Heidelberg Berlin; 2003, p. 55; table 3.2.

The oligopeptides according to the invention are suitable for topical application to the skin. Oligopeptides are well tolerated by human skin and can have good bioavailability. Moreover, oligopeptides can exhibit good effectiveness for increasing skin sensitivity and improving perception.

There is a need, especially with regard to the regeneration of reduced or lost power of perception via the skin sensory organ, for example, as a result of damage or previous illnesses, for novel, effective dermatological compositions. Weakened or impaired sensory perception via the skin can, in the long term, adversely affect the well-being, for example as a result of a feeling of numbness.

The oligopeptides according to the invention can advantageously be used in dermatological compositions for topical application in people whose perception via the skin is reduced, impaired or at least temporarily lost, for example, as a result of damage or previous illnesses. This may, for example, be patients with scars, burns, injuries. It is also known that in stroke patients perception, i.e., for example, sensitivity to hot and cold, via the skin can at least temporarily stop.

Use of the oligopeptides according to the invention in dermatological compositions can bring about more rapid restoration of the receptions via the skin and thus prevent her damage to the skin. This restoration of the skin sensation and perception, moreover, makes a considerable contribution to an improved general feeling and to more rapid rehabilitation of such patients.

The oligopeptides employed in this invention can be obtained simply and cost effectively in the required purity via the classic routes of peptidic synthesis, for example, by automated solid-phase synthesis over Merrifield resins or via enzymatic routes. The person skilled in the art in the field of peptidic synthesis likewise knows how derivatives according to the invention of the oligopeptides can be produced using known methods.

In a preferred embodiment, the oligopeptide or derivative has a naturally occurring amino acid sequence. For the purposes of the invention, "naturally occurring" means that the amino acid sequence of the oligopeptide occurs completely or as the bioactive part of an overall sequence in nature or in natural products, for example, in grapes or in wine or juice from grapes. The oligopeptides employed in the invention can be produced synthetically according to their natural models, or the oligopetides can be obtained directly from the corresponding natural sources, for example, by extraction.

One advantage is that these oligopeptides used according to the invention can have particularly good activity and bioavailability and are in principle highly compatible, toxicologically acceptable and biodegradable.

The use of the pentapeptide with the amino acid sequence Val-Glu-Ile-Pro-Glu (SEQ ID NO:2) and/or Tyr-Pro-Ile-Pro-Phe (SEQ ID NO:3) has proven particularly suitable according to the invention for increasing skin sensitivity and neuronal perception. These oligopeptides according to the invention exhibit a particularly good activating, stimulating effect for perception via the skin.

In a further preferred embodiment, to derivatize the oligopeptides used according to the invention through amide bonding, an alkylic lipophilic chain or an arylic radical or their alkyloxic or aryloxic or alkylaryloxic variant can be attached to the N-terminal end of the oligopeptide and/or to the C-terminal end, by ester bonding an alkylic alcohol or by amide bonding an $NH_2$ group or such an N-alkylically substituted group.

According to the invention, an acyl group can preferably be arranged on the N-terminal end of the amino acid sequence. This can optionally carry branched or straight-chain, long-chain or short-chain, saturated or unsaturated radicals, and be unsubstituted or substituted by one or more hydroxyl, amino, acylamino, sulfate or sulfide groups, Such N-acylic derivatives can be produced, for example, with acetic acid, biotinic acid, caprylic acid, capric acid, lauric acid, myristic acid, octanoic acid, palmitic acid, stearic acid, behenic acid, linoleic acid, linolenic acid, lipoic acid, oleic acid, isostearic acid, elaidic acid, 2-ethylhexanoic acid, coconut oil fatty acid, tallow fatty acid, hydrogenated tallow fatty acid, palm kernel oil fatty acid, lanolin fatty acid or mixtures thereof Preferred acyl groups include substituted or unsubstituted acetyl, palmitoyl, elaidoyl, myristyl, biotinyl and octanoyl groups.

Peptide sequences suitable according to the invention include:
Ala-Ile-Pro-Gln (SEQ ID NO.4)
Gly-Pro-Ile-Pro (SEQ ID NO.5)
octanoyl-Ser-His-Pro-Ile (SEQ ID NO.6)
Arg-Lys-Pro-Ile-Pro (SEQ ID NO.7)
Tyr-Pro-Ile-Ser-Leu (SEQ ID NO.8)
palmitoyl-Gly-His-Pro-Ile-Ser (SEQ ID NO.9)
Gly-Val-Glu-Ile-Pro-Ala (SEQ ID NO.10)
hexanoyl-Thr-Lys-Pro-Ile-Pro-Arg (SEQ ID NO.11)

For the purposes of the invention, particular preference is given to the N-palmitoyl derivatives, in particular, N-palmitoyl-Val-Glu-Ile-Pro-Glu (SEQ ID NO:2) and/or N-palmitoyl-Tyr-Pro-Ile-Pro-Phe SEQ ID NO:3).

It is particularly advantageous that, through such a modification and derivatization, the lipophilicity of the oligopeptide can be increased, and thus a higher affinity to the epidermis and a considerably improved penetration capacity can be obtained. The biological effect of the oligopeptide can thus be significantly increased.

In some embodiments, dermatological compositions including at least one oligopeptide with a sequence of 4, 5 or 6 amino acids or a derivative thereof for increasing the sensitivity of the skin and for supporting and improving the perception of the skin are provided, where an Ile-Pro motif and/or a Pro-Ile motif is present in the oligopeptide.

For the purposes of the invention, dermatological compositions preferably include pharmaceutical compositions and medicaments which are preferably applied topically. Optionally, the dermatological compositions can simultaneously serve a number of purposes and also serve for cosmetic purposes and/or for the provision of one or more additional pharmaceutical compositions.

According to the invention, an oligopeptide with a sequence of 4, 5 or 6 amino acids or a derivative thereof with an Ile-Pro motif and/or a Pro-Ile motif may be present in the dermatological composition. However, it is also possible to use a mixture of two or more oligopeptides and/or one or more of its derivatives. It is likewise possible to use different oligopeptide derivatives in a mixture with one another.

In a further preferred embodiment of the invention, an oligopeptide according to the invention or derivatives thereof which have a naturally occurring amino acid sequence can be used in the dermatological composition. Such compositions exhibit good bioavailability of the active ingredient and good dermatological compatibility.

The pentapeptides with the amino acid sequence Val-Glu-Ile-Pro-Glu (SEQ ID NO:2) and/or Tyr-Pro-Ile-Pro-Phe (SEQ ID NO:3), which may be present, for example, in wine, have proven to be particularly effective for stimulating perception in the skin.

In another embodiment, the dermatological composition can comprise derivatives, preferably acyl derivatives, of the oligopeptide suitable according to the invention. In this connection, particular preference is given to an oligopeptide suitable according to the invention which has been derivatized with substituted or unsubstituted acetyl, hexanoyl, myristyl, palmitoyl and/or biotinyl groups.

As a result of such a modification and derivatization, the lipophilicity of the oligopeptide can be increased in order to obtain a higher affinity to the epidermis and a considerably improved penetration capability. As a result of such a measure, the biological effect of the oligopeptide suitable according to the invention can be significantly increased. The use according to the invention of the pentapeptides with the amino acid sequence N-palmitoyl-Val-Glu-Ile-Pro-Glu (SEQ ID NO:2) and/or N-palmitoyl-Tyr-Pro-Ile-Pro-Phe (SEQ ID NO:3) has proven particularly effective for stimulating perception.

An advantage here is that the required concentration of oligopeptide in order to achieve the desired effect in the dermatological composition can be considerably reduced as a result of the improved properties.

The dermatological composition of the invention comprises at least one oligopeptide and/or derivative thereof in an active ingredient amount between 0.0005% by weight and 2% by weight, preferably between 0.01% by weight and 1% by weight, and more preferably between 0.05% by weight and 0.5% by weight, based on the weight of the total composition.

In principle, the amount of oligopeptide used as active ingredient in the total composition is such that the desired increase in the skin sensitivity can be achieved.

Unless stated otherwise, the quantitative data in the present description are given in percent by weight (% by wt.) based on the total amount of the dermatological composition.

In one embodiment of the invention, the dermatological composition comprises the oligopeptide and/or a derivative thereof in a suitable carrier substance or a suitable carrier system comprising two or more carrier substances.

The dermatological compositions can be formulated, for example, as oil-in-water (O/W) emulsions, water-in-oil (W/O) emulsions, water-in-silicone emulsions, multiple emulsions (for example, W/O/W or O/W/O), Oil-in-water-in-silicone emulsions, microemulsions, nanoemulsions, PIT emulsions, Pickering emulsions, suspensions, dispersions, hydrogels, lotions, gels, lipogels, single-phase or multiphase solutions, foams, plasters, creams, ointments, pastes, powders and/or as other customary topical formulations, which can be administered, for example, also via sticks, masks or as sprays.

In further embodiments of the invention, in addition to the oligopeptides and/or their derivatives or mixtures thereof, various other and additional active and/or functional constituents may be present which are customarily used in topical and/or transdermal pharmaceutical and/or cosmetic skin products or bodycare products.

These may be, for example, fats, oils, waxes, silicones, emulsifiers, alcohols, polyols, thickeners, swelling agents, structure regulators, consistency regulators, moisturizing or humectant substances, surfactants, softening substances (emollients), foam suppressants, anionic, cationic or amphoteric polymers, alkalizing or acidifying agent, buffer substances, pH regulators, stabilizers, softeners, adsorbents, astringents, photoprotective agents, film formers, electolytes, sequestrants, water, organic solvents, preservatives, stabilizers, antimicrobial and biocidal substances, bactericides, antioxidants, pharmaceuticals, vitamins, complexing agents, enzymes, fragrances, aromas or dyes. This list is only exemplary and is not to be regarded as exhaustive.

Further constituents and substances for dermatological compositions are known to the person skilled in the art and can be found in the prior art, for example, including WO 2005/048968.

An oligopeptide suitable according to the invention is preferably formulated with one or more dermatologically compatible additives and auxiliaries. According to the invention, these are understood as meaning pharmaceutically and cosmetically compatible substances which are suitable for use in contact with the human skin, inter alia with regard to toxicity, incompatibilities, skin irritations and allergic reactions.

According to the invention, preference is given to selecting those additives and auxiliaries which have a positive influence on the desired effect of the oligopeptides in the dermatological composition and/or its applicability. Advantageously, the oligopeptides according to the invention can be readily combined with customary additives and auxiliaries and can be incorporated without problems into customary and/or approved dermatological guide formulations.

In a further embodiment of the present invention, the oligopeptides and/or their derivatives can be dissolved prior to being introduced into the overall composition. The peptides can, for example, be dissolved in general in classic cosmetic or skin pharmacological solvents, such as ethanol, propanol or isopropanol, glycol propylene, glycerol, butylene glycol, ethoxy diglycol, polyethylene glycol, methyl ethers or diglycol ethylenes, cyclic polyols, ethoxylic or propoxylic diglycols or any mixtures of these solvents. Methods for solubilizing oligopeptides are known to the person skilled in the art. The oligopeptides or their derivatives can also be introduced or encapsulated beforehand into dermatopharmaceutical or cosmetic vectors (transport systems), for example, liposomes, chylomicrones, macro, micro- or nanoparticles, and macro-, micro- or nanocapsules, or be absorbed or adsorbed onto pulverulent, organic polymers, talcs, bentonite, silicon dioxide or other mineral media.

These solutions or preparations can then be used in all possible galenic, skin pharmacological formulations.

For example, by producing O/W nanoemulsions as colloidal carrier system with sparingly water-soluble medicaments, it is possible to improve the penetration and permeation through the skin and thus to increase the bioavailability of the active ingredients.

A dermatological composition of the present invention can, moreover, comprise an effective amount of a penetration accelerator, a so-called "enhancer", which is able to promote the transport of active ingredient through and/or into the skin.

Solvents such as alcohols, alkylmethyl sulfoxides and polyols increase primarily the solubility and have a favorable influence on the partition coefficients. Furthermore, some solvents such as dimethylsulfate (DMSO) or ethanol can extract epidermal lipids and thus increase the permeability of the horny layer. Oleic acid, azones (epsilon-laurocapram) and isopropyl myristate are typical examples of penetration accelerators which are incorporated in an intercalatory manner into the lipid double layers of the skin and disturb their tight packing, as a result of which the diffusion rate can be increased. Ionic surfactants, decylmethyl sulfoxide, DMSO or urea loosen up the solid protein structure in the horny cells and the diffusion coefficient increases.

Described in the text below are examples of abovementioned additional dermatological active ingredients, additives and auxiliaries which can be incorporated in combination with the oligopeptides into dermatological compositions according to the invention. Examples in the course of the description only serve to further illustrate the invention and are nonlimiting for this.

In the dermatological compositions of the invention, the described materials and substances can perform one or more functions and/or have one or more pharmaceutical and/or cosmetic effects.

For the additional care and for the protection of the skin, the dermatological compositions of the present invention can advantageously comprise creatine, ceramides, pseudoceramides, protein hydrolyzates of vegetable or animal origin based on keratin, collagen, elastin, wheat, rice, soybean, milk, silk, corn, amino acid and amino acid derivatives, polyaspartic acid (derivatives), antiinflammatory active ingredients, antimicrobial active ingredients, customary antioxidants, vitamins, dexpanthenol, retinol, niacinamide, lactic acid, pyrrolidonecarboxylic acid, bisabolol, and plant, yeast and algae extracts.

In synergy with the oligopeptides according to the invention, these can, for example, have a wound healing-promoting, moisturizing antiwrinkle or anticellulite effect and be used as skincare constituents.

Such compositions can, for example, be used in the aftertreatment of wounds and scars and additionally, besides the restoration of and/or improvement in skin sensitivity and neuronal perception of stimuli via the skin, can also achieve good results with regard to the healing and restoration of skin tissue through the action of the oligopeptides according to the invention.

This combined action can be particularly advantageous if the skin tissue has been damaged through injury and/or burning.

Typical guide formulations for skin-treatment compositions belong to the known prior art and are contained, for example, in the brochures of the manufacturers of the particular base materials and active ingredients. An informative source on the type and preparation of such formulations is, for example, the annually published Kosmetik-Jahrbuch (Editor: B. Ziolkowsky, Verlag für Chemische Industrie). Moreover, reference may also be made to Nowak G. A., "Die Kosmetischen Präparate" [Cosmetic preparations] (for example volume 2 "Die kosmetischen Präparate—Rezeptur, Rohstoffe, wissenschaftliche Grundlagen" [Cosmetic preparations—formulation, raw materials, scientific principles]) Verlag für Chemische Industrie, Editor: Ziolkowski. Reference is likewise made to "The Chemistry and Manufacture of Cosmetics", Volume II—Formulating (3rd edition, Allured Publishing Corporation).

Advantageously, known formulations of dermatological compositions can generally be adopted unchanged. If necessary, however, the desired modifications for adaptation and/or optimization can be undertaken through simple measures known to the person skilled in the art.

Examples of formulations according to the invention with a dermatologically effective composition are listed below. The products listed in the tables below are obtainable:

*[1] = ABIL ® Care 85 obtainable from Goldschmidt GmbH
*[2] = TEGINACID ® C obtainable from Goldschmidt GmbH
*[3] = TEGIN ® M obtainable from Goldschmidt GmbH
*[4] = TEGO ® Alkanol 1618 obtainable from Goldschmidt GmbH
*[5] = TEGO ® Carbomer 134 obtainable from Goldschmidt GmbH
*[6] = TEGOSOFT ® OP obtainable from Goldschmidt GmbH
*[7] = TEGO ® Care PS obtainable from Goldschmidt GmbH
*[8] = TEGO ® Alkanol 18 obtainable from Goldschmidt GmbH
*[9] = TEGOSOFT ® liquid obtainable from Goldschmidt GmbH
*[10] = TEGOSOFT ® CT obtainable from Goldschmidt GmbH
*[11] = TEGO ® Care 450 obtainable from Goldschmidt GmbH
*[12] = TEGOSOFT ® OS obtainable from Goldschmidt GmbH
*[13] = TEGOSOFT ® DO obtainable from Goldschmidt GmbH
*[14] = TEGO ® Carbomer 141 obtainable from Goldschmidt GmbH
*[15] = TEGOSOFT ® PC 41 obtainable from Goldschmidt GmbH
*[16] = ABIL ® B 8851 obtainable from Goldschmidt GmbH
*[17] = Euxyl K 400 obtainable from Schülke & Mayr
*[18] = TEGO ® Carbomer 140 obtainable from Goldschmidt GmbH
*[19] = Macrogol 6000 obtainable from Sasol
*[20] = HyaCare obtainable from Goldschmidt GmbH

FORMULATION EXAMPLE 1 ACCORDING TO THE INVENTION

Oligopeptide-Containing Skincare Cream

| | | Oligopeptide-containing skincare cream | |
|---|---|---|---|
| A) | ABIL ® Care 85*[1] | (Bis-PEG/PPG-16/16 PEG/PPG-16/16 dimethicone; caprylic/capric triglycerides) Ceteareth-25 Glyceryl stearate | 1.5% by wt. |
| | TEGINACID ® C*[2] | Cetearyl alcohol | 0.5% by wt. |
| | TEGIN ® M*[3] | | 2.0% by wt. |
| | TEGO ® alkanol 1618*[4] | | 6.0% by wt. |
| | Cyclomethicone | | 5.0% by wt. |
| B) | Glycerol | | 3.0% by wt. |
| | Water | | 79.25% by wt. |
| | N-octanoyl Val-Gln-Ile-Pro-Glu (SEQ ID NO: 2) | | 0.005% by wt. |
| C) | TEGO ® Carbomer 134*[5] | Carbomer | 0.15% by wt. |
| | TEGOSOFT ® OP*[6] | Ethylhexyl palmitate | 0.6% by wt. |
| D) | NaOH (10%) | | q.s. |
| | Perfume | | q.s. |
| | Preservative | | q.s. |

Preparation of the Formulation

Phase A) and B) were heated to 75° C. Phase A) was then added with stirring to B) and homogenized, for example using an Ultra Turrax. The emulsion was cooled with gentle stirring to 60° C. At 60° C., phase C) was added and the mixture was briefly homogenized again. The mixture was cooled with stirring and, below 40° C., phase D) was added.

FORMULATION EXAMPLE 2 ACCORDING TO THE INVENTION

Oligopeptide-Containing O/W Cream

| Oligopeptide-containing O/W cream | | |
|---|---|---|
| A) TEGO ® Care PS*[7] | Methyl glucose sesquistearate Stearyl alcohol | 3.0% by wt. |
| TEGO ® Alkanol 18*[8] | Glyceryl stearate | 1.5% by wt. |
| TEGIN ® M*[3] | Cetearyl ethylhexanoate | 3.5% by wt. |
| TEGOSOFT ® liquid*[9] | Caprylic/capric triglyceride | 9.2% by wt. |
| TEGOSOFT ® CT*[10] | | 10.0% by wt. |
| B) Glycerol | | 3.0% by wt. |
| Water | | 62.65% by wt. |
| Oligopeptide Tyr-Pro-Ile-Pro-Phe (SEQ ID NO: 3) | | 0.01% by wt. |
| C) TEGO ® Carbomer 134*[5] | Carbomer | 0.2% by wt. |
| TEGOSOFT ® liquid*[9] | Cetearyl ethylhexanoate | 0.8% by wt. |
| Active ingredient combination 1 | | 5.0% by wt. |
| NaOH (10%) | | 0.65% by wt. |
| Perfume | | 0.5% by wt. |
| Preservative | | q.s. |

Preparation of the Formulation

Phase A) and B) were heated to 65° C. Phase B) was then added to A) and homogenized, for example using an Ultra Turrax. The emulsion was cooled to 60° C. with gentle stirring. At 60° C., phase C) was added and the mixture was briefly homogenized again. The active ingredient combination 1 and also the sodium hydroxide solution and the perfume oil were added one after the other at 35 to 40° C.

FORMULATION EXAMPLE 3 ACCORDING TO THE INVENTION

O/W Lotion with Oligopeptide

| O/W lotion with oligopeptide | | |
|---|---|---|
| A) TEGO ® Care 450*[11] | Polyglyceryl-3 methylglucose distearate Ethylhexyl stearate | 2.0% by wt. |
| TEGOSOFT ® OS*[12] | Decyl oleate | 7.2% by wt. |
| TEGOSOFT ® DO*[13] | | 5.0% by wt. |
| B) Glycerol | | 3.0% by wt. |
| Water | | 81.3% by wt. |
| Oligopeptide Pro-Ile-Pro-Phe (SEQ ID NO: 12) | | 0.1% by wt. |
| C) TEGO ® Carbomer 141*[14] | Carbomer | 0.2% by wt. |
| TEGOSOFT ® OS*[12] | Ethylhexyl stearate | 0.8% by wt. |
| D) NaOH (10%) | | 0.65% by wt. |
| E) Perfume, Preservative | | q.s. |

Preparation of the Formulation

Phase A) and B) were heated separately to 80° C. Phase A) was then added to B) without stirring and homogenized, for example using an Ultar Turrax. The emulsion was cooled to 60° C. with gentle stirring. At 60° C., phase C) was added and the mixture was briefly homogenized again. The emulsion was cooled to below 40° C. with gentle stirring. Phase D) was then added.

FORMULATION EXAMPLE 4 ACCORDING TO THE INVENTION

Oligopeptide-Containing Clear Hydrogel

| Oligopeptide-containing clear hydogel | | |
|---|---|---|
| A) TEGOSOFT ® PC 41*[15] | Polyglyceryl-4 caprate PEG/PPG-14/4 dimethicone | 1.0% by wt. |
| ABIL ® B 8851*[16] | Methyldibromo glutaronitrile, phenoxyethanol | 7.2% by wt. |
| Euxyl K 400*[17] | | 0.15% by wt. |
| Glycerol | | 3.0% by wt. |
| Perfume | | 0.2% by wt. |
| B) TEGO ® Carbomer 140*[18] | Carbomer | 0.2% by wt. |
| TEGO ® Carbomer 141*[14] | Carbomer | 0.3% by wt. |
| Water | | 49.5% by wt. |
| C) Water | | 32.5% by wt. |
| Macrogol 6000*[19] | PEG-150*[19] | 1.0% by wt. |
| Hexanoyl-Thr-Lys-Pro-Ile-Pro-Arg (SEQ ID NO: 11) | | 0.0005% by wt. |

| -continued | | |
|---|---|---|
| Oligopeptide-containing clear hydogel | | |
| D) NaOH (10%) | | 1.6% by wt. |
| E) HyaCare*[20] | Sodium hyaluronate | 0.1% by wt. |
| Water | | 9.9% by wt. |

Preparation of the Formulation

The raw materials of phase A) were mixed in the order given. Phase B) was then added with stirring. Phase C) was then added with stirring. Phase D) was then added with stirring. Finally, phase E) was added and the mixture including phases A-E was stirred until the formulation was clear.

The skin pharmacological effect of the peptides according to the invention was demonstrated in an "in vivo test series":

For the effectiveness studies described below, a simple O/W cream was used which had the following composition:

Oligopeptide Containing Dermatological Composition

| Oligopeptide containing dermatological composition | |
|---|---|
| Ceteareth-25 | 2.0% by wt. |
| Glyceryl stearate | 4.0% by wt. |
| Stearyl alcohol | 2.0% by wt. |
| Ethylhexyl stearate | 8.5% by wt. |
| Caprylic/capric triglyceride | 8.5% by wt. |
| Preservative | 0.1% by wt. |
| Water | 74.8% by wt. |
| Oligopeptide Val-Glu-Ile-Pro-Glu (SEQ ID NO: 2) | 0.1% by wt. |

Ten volunteers were selected for the test. Over a period of 10 days, each person applied a defined amount of the oligopeptide-containing O/W cream twice daily to the left volar forearm. As control, an equivalent amount of base cream without added oligopeptide was applied to the right forearm. Attached to each upper arm on each of the subjects was a heat sensor with an inbuilt thermometer, with which a defined area of the skin was heated and then the temperature was measured. The subjects indicated when the predefined threshold for "lukewarm", "warm", "very hot" and "painfil" was exceeded. After establishing these sensations and their respective sensation thresholds, the subjects applied the dermatological composition which comprises the oligopeptide according to the invention to be tested in the measurement area on the skin. After various waiting times, the threshold values for the heat sensation were determined again in the same way. In this way it was possible to test an increase in the skin sensitivity or increase in neuronal perception of the skin compared with the same dermatological composition which did not contain the oligopeptide.

The effectiveness of the oligopeptides according to the invention was demonstrated in this test: an increase in the heat sensation on the left forearm treated with the O/W cream containing the oligopeptide was noticeable after 30 minutes and was considerable after 2 hours.

It can be demonstrated with this test that the skin sensitivity and perception can be increased through the dermatological composition according to the invention, and that the composition of the present invention is suitable for stimulating skin sensation and perception.

The dermatological compositions can be used, for example, in the medical treatment of scar tissue or concomitantly in the therapy of patients who have lost the ability to perceive stimuli via the skin, for example, as the result of a stroke, or whose skin sensitivity has been reduced or impaired by other injuries or previous illnesses.

The dermatological compositions can, for example, also be used for the cosmetic treatment of aging phenomena of the skin and counteract a diminishment of their function-bearing component, such as reduced neuronal perception of the skin. As a result of the application of dermatological compositions according to the invention, the skin feel and thus also the general well-being can be considerably improved and positively influenced.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method of increasing the sensitivity of skin comprising applying a dermatological composition comprising at least one oligopeptide consisting of Val-Glu-Ile-Pro-Glu (SEQ ID NO: 2) or Tyr-Pro-Ile-Pro-Phe (SEQ ID NO: 3), or the N-palmitoyl derivatives thereof, to the skin of a patient experiencing weakened or impaired sensory perception via the skin wherein after said applying the skin has a greater sensitivity.

2. The method of claim 1, wherein the at least one oligopeptide is the N-palmitoyl derivative of Val-Glu-Ile-Pro-Glu (SEQ ID NO:2) or Tyr-Pro-Ile-Pro-Phe (SEQ ID NO:3).

3. The method of claim 1, wherein the at least one oligopeptide is present in the dermatological composition at a concentration between 0.0005% by weight and 2% by weight, based on the weight of the total composition.

4. The method of claim 1, wherein the dermatological composition further comprises one or more dermatologically compatible additives and/or auxiliaries.

5. The method of claim 4, wherein at least one of the dermatologically compatible additives and/or auxiliaries is a carrier substance.

6. The method of claim 1, wherein the dermatological composition further comprises one or more pharmaceutically and/or cosmetically effective substances.

7. The method of claim 1, wherein the dermatological composition is in the form of an emulsion.

8. The method of claim 7, wherein said emulsion is selected from the group consisting of oil-in-water (O/W) emulsions, water-in-oil (W/O) emulsions, water-in-silicone emulsions, multiple emulsions, oil-in-water-in-silicone emulsions, microemulsions, nanoemulsions, PIT emulsions, Pickering emulsions, suspensions, and dispersions.

9. The method of claim 8, wherein said multiple emulsions are selected from water-in-oil-in-water (W/O/W) or oil-in-water-in-oil (O/W/O) emulsions.

10. The method of claim 1, wherein the weakened or impaired sensory perception via the skin is the result of scars, burns, injuries or stroke.

* * * * *